United States Patent
Taylor et al.

(10) Patent No.: US 6,375,817 B1
(45) Date of Patent: Apr. 23, 2002

(54) APPARATUS AND METHODS FOR SAMPLE ANALYSIS

(75) Inventors: Todd A. Taylor, Framingham; William W. Carson, Hopkinton; Lance Koutny, Methuen, all of MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 0 days.

(21) Appl. No.: 09/293,313

(22) Filed: Apr. 16, 1999

(51) Int. Cl.[7] .................. G01N 22/26; G01N 27/447
(52) U.S. Cl. .................. 204/453; 204/604; 422/100; 436/180
(58) Field of Search .................. 210/198.2, 101, 210/243, 656; 204/600, 601, 602, 603, 604, 605, 450, 451, 452, 453, 455; 422/100; 436/180

(56) References Cited

U.S. PATENT DOCUMENTS

| | | | |
|---|---|---|---|
| 4,315,754 A | 2/1982 | Ruzicka et al. ............ | 422/81 X |
| 4,426,451 A | 1/1984 | Columbus ................... | 436/518 |
| 4,683,195 A | 7/1987 | Mullis et al. ................ | 435/6 |
| 4,906,344 A | 3/1990 | Hjerten ........................ | 204/451 |
| 4,960,566 A | 10/1990 | Mochida ...................... | 422/65 |
| 4,979,365 A | 12/1990 | Baker .......................... | 60/528 |
| 5,240,576 A | 8/1993 | Lauer et al. ................ | 204/451 |
| 5,273,907 A | 12/1993 | Malmquist ................... | 436/165 |
| 5,287,758 A | 2/1994 | Geiss et al. ................ | 422/922 X |
| 5,302,264 A | 4/1994 | Welch et al. ................ | 204/452 |
| 5,304,487 A | 4/1994 | Wilding et al. ............... | 435/29 |
| 5,316,954 A | 5/1994 | Hupe et al. ................... | 436/89 |

(List continued on next page.)

FOREIGN PATENT DOCUMENTS

| | | | |
|---|---|---|---|
| CA | 2058648 | | 7/1992 |
| EP | 0 608 120 | | 7/1994 |
| WO | WO 93/22053 | | 11/1993 |
| WO | WO 93/22054 | | 11/1993 |
| WO | WO 93/22058 | | 11/1993 |
| WO | WO 96/04547 | * | 2/1996 |
| WO | WO 97/22825 | | 6/1997 |

OTHER PUBLICATIONS

Chapter 6: Qualitative and Quantitative Analysis in "Capillary Electrophoresis: Principles and Practice," Kuhn et al., eds., (Springer–Verlag, New York) sections 6.1 and 6.2, pp. 243–249 (1993).

*Primary Examiner*—Jill Warden
*Assistant Examiner*—John S. Starsiak, Jr.
(74) *Attorney, Agent, or Firm*—Testa, Huwitz & Thibeault, LLP

(57) ABSTRACT

The present invention is directed to apparatus and methods for rapid, automated, microscale sample analysis using pressure differentials. The invention includes an apparatus having intersecting channels for introduction of a sample and separation of that sample into its components. The sample introduction and separation channels preferably are etched in a microfabricated device, such as a microchip, to form a junction. Pressure gradients are applied to the channels to form a sample plug in the separation channel. The separation channel may have disposed within it a medium for separation of the components suspected to be contained in the sample. For example, with the proper medium, a voltage gradient may be applied along the separation channel to separate the components of the sample electrophoretically. The apparatus also may include means for detecting the components of the sample subsequent to separation.

17 Claims, 7 Drawing Sheets

U.S. PATENT DOCUMENTS

| | | | |
|---|---|---|---|
| 5,500,071 A | * | 3/1996 | Kaltenbach et al. . 210/198.2 X |
| 5,565,171 A | | 10/1996 | Dovichi et al. ............. 422/68.1 |
| 5,624,850 A | | 4/1997 | Kumar et al. ................ 436/527 |
| 5,645,702 A | | 7/1997 | Witt et al. ................... 204/501 |
| 5,646,048 A | | 7/1997 | Templin et al. ............. 436/180 |
| 5,650,846 A | | 7/1997 | Yin et al. ................ 204/603 X |
| 5,720,923 A | | 2/1998 | Haff et al. .................. 422/68.1 |
| 5,750,015 A | | 5/1998 | Soane et al. ................. 204/454 |
| 5,779,868 A | | 7/1998 | Parce et al. ................. 204/604 |
| 5,900,130 A | | 5/1999 | Benvegnu et al. .......... 204/453 |
| 5,976,336 A | * | 11/1999 | Dubrow et al. ............. 204/453 |
| 6,086,740 A | * | 7/2000 | Kennedy .................... 204/601 |

* cited by examiner

APPARATUS AND METHODS FOR SAMPLE ANALYSIS

FIELD OF THE INVENTION

The present invention relates to apparatus and methods for sample analysis. More specifically, the invention is directed to apparatus and methods for sample plug formation and subsequent separation and/or analysis.

BACKGROUND OF THE INVENTION

Methods for conducting and analyzing microscale chemical reactions often require multiple steps and extensive handling of reagents. These methods typically are labor intensive and involve complex combinations of instrumentation, e.g., pipettes, pumps, syringes, valves, tubing, reagent vessels, and reaction chambers. Such complexities may contribute to inaccuracies, increased costs and reduced reaction yields.

Analytical techniques typically require a high degree of labor and the use of complex apparatus. Moreover, many laboratory and industrial chemical processes involve the use of relatively large volumes of reagents and multiple laboratory instruments. Typical large scale immunoassays, e.g., require the use of pipettes, reagent vessels, and reaction chambers. See, e.g., Mattiasson et al., *Proc. Int. Symp. on Enzyme-Labeled Immunoassay of Hormones and Drugs*, (Pal, S., Ed., Walter de Gruyter, Berlin (1978), p. 91). Such processes, regardless of the size of the reaction, also may require multiple steps. Accordingly, there is a potential for reduced accuracy due to the introduction of impurities, volumetric inaccuracies, and low reproducibility. These problems especially are acute in microscale diagnostic applications in which biological samples are analyzed, such as, e.g., immunoassays, polynucleotide amplifications, or hybridizations.

Recently, efforts have been made to streamline chemical processes to reduce costs, increase accuracy, and improve reaction yields. For example, capillary electrophoresis techniques have been proposed to increase resolution in immunoassays. Various attempts have been made to enhance other common analytical techniques, such as the polymerase chain reaction (PCR). For example, U.S. Pat. No. 5,273,907 reports a capillary pre-loaded with PCR reagents which is used to deliver a sample to the reagents for DNA amplification. Similarly, International Patent Publication WO 93/22058 describes a micro-scale device for performing PCR In this case, PCR reagents from a first chamber are mixed with sample in a second chamber by movement of materials through channels in a microchip.

Recently, efforts have been made to streamline chemical processes to reduce labor and complexity. One such effort involves the use of microchip assemblies. A microchip assembly typically consists of a thin silica substrate or other polymeric substrate onto which channels are etched. The channels serve as means for reagent transport and/or as the reaction chambers themselves. Microchip assemblies for performing micro-scale chemical reactions may comprise a series of interconnected channels. For example, channels may be etched onto the surface of a microfabricated solid. Reagents in solution then are placed into the channels, and allowed to react with, e.g., reagents already in the channels. Voltage gradients may be used to control sample flow and mixing. See, e.g., International Publication WO 96/04547. Hydrogen and oxygen gas often results from use of voltage gradients to control sample flow. Electrolysis products also may accumulate near the electrode surface.

Microchip assemblies which do not require voltage gradients to inject the samples and solutions have been designed. See, e.g., U.S. Pat. No. 5,304,487; International Publication WO 93/22053; and International Publication WO 93/22054 (describing microchip assemblies for sample analysis). In such systems, a steady flow of liquid is pumped through a series of channels etched on a microchip. Sample is introduced through one of the channels and is mixed with the flow of liquid. These systems are used to detect the presence of a sample component or the presence of some biological entity (a bacterium or virus, e.g.) by measuring the variance in flow rate between liquid and liquid mixed with sample as each flows through the microchip.

There remains a need in the art for methods and devices which will decrease the time, labor, costs, biohazard exposure and complexity currently involved in the performance of chemical analysis of microscale biological samples. More particularly there exists a need for apparatus and methods which efficiently and economically form and deliver a sample plug to a separation channel and/or analytical device.

SUMMARY OF THE INVENTION

Apparatus and methods have been developed for rapid, automated analysis of microscale samples using pressure differentials. A sample plug formation device of the invention generally comprises two intersecting channels, an introduction channel and a separation channel. A sample is introduced through an opening in a first channel, referred to herein as a sample introduction channel. The sample moves through the sample introduction channel by vacuum, pressure, capillary action, or a combination thereof. At a distance from the point of sample introduction, the sample introduction channel forms a juncture or junction with (i.e., intersects) a second channel, referred to herein as a separation channel. Through the use of pressure and/or vacuum applied to the separation channel and/or the sample introduction channel, a portion of the sample is transported into the separation channel as the bulk sample crosses the junction between the sample introduction and separation channels. With the proper control, a discrete plug of sample reproducibly may be formed in the separation channel and subjected to separation techniques and/or analysis. Subsequent to the formation of the sample plug, the portion of sample which does not form the sample plug typically is moved to a waste outlet.

Formation of the sample plug at the channel junction is controlled by application of pressure differentials in and between the sample introduction and separation channels. A first pressure differential is applied so as to induce sample flow through the introduction channel to the juncture. Subsequently, at least a second pressure differential is applied to move a portion of the sample into and along the axis of the separation channel. A plug of sample generally is formed in the separation channel at the junction when pressure is increased axially along the separation channel relative to the sample introduction channel. The frequency and size of plug formation is controlled by controlling the pressure differentials.

The sample introduction and separation channels may be capillaries formed to intersect at a junction. A preferred structure defining the sample introduction and separation channels is a microfabricated solid, such as a microchip. Typically, channels are etched directly into the microchip. In a preferred embodiment, the microchip comprises a series of sample introduction and separation channels etched onto its surface. Such channels preferably have cross-sectional dimensions of between about 0.1 $\mu$m and about 1000 $\mu$m.

In a preferred embodiment, the separation channel comprises a longitudinal axis containing a medium, e.g., water, an electrolyte, or a polyacrylamide solution or gel, which aids the separation of components suspected to be in the sample. Thus, a sample plug that is formed at the junction of the sample introduction and separation channels migrates axially along the separation channel where it may be separated into its components. Preferably, the sample introduction and separation channels contain a buffer that is compatible with the sample and separation medium, if present. The device may further comprise a voltage generator for applying a voltage axially along the longitudinal axis of the separation channel. The application of a voltage along the separation channel may aid in the separation of components of the sample, e.g., when the separation is accomplished by electrophoresis.

Also in a preferred embodiment, a device of the invention comprises a detector. The detector is placed in proximity to the separation channel for detecting separated components of a sample. The detector may include an ultraviolet detector, a visible light detector, an infrared detector, a fluorescence detector, a chemilumenescence detector, a refractive index detector, a Raman detector, a mass spectrometer, an electrochemical detector and/or a conductivity detector. Preferably, the detector is a mass spectrometer, a fluorescence detector, or radioactivity detector.

A sample plug formation device of the invention may be used in conjunction with a sample delivery system. A preferred sample delivery system is disclosed in co-owned, co-pending U.S. patent application Ser. No. 09/293,314, entitled "Apparatus And Methods For Sample Delivery," which is incorporated by reference herein. In a preferred embodiment of the application, a chemical reaction takes place in a sample delivery system, and the products of the reaction are charged to a sample introduction channel of a device of the present invention.

A preferred sample delivery device has a housing defining a capillary which has an open end for introduction of a sample and a closed end. The closed end preferably is associated with a temperature control device which is used to control movement of sample and reactants into the sample delivery system. Immobilized within the capillary may be chemical reagents, such as, binding proteins, ligands, receptors, antibodies, or antigens. These reagents may be detectably labeled and, preferably, are fluorescently labeled. These reagents also may be chemically or enzymatically labelled, e.g., to permit amplification prior to detection.

The present invention provides for rapid, accurate, and reproducible analysis of microscale samples. When used in conjunction with a sample delivery device as described above, the analysis of a sample is an automated process from start to finish. Moreover, the automated process may include one or more reactions which may occur within the sample delivery device. The invention will be understood further upon consideration of the following drawings, description, and claims.

DESCRIPTION OF THE DRAWINGS

Like reference characters in the respective drawn figures indicate corresponding parts.

DETAILED DESCRIPTION OF THE INVENTION

Figure 1:
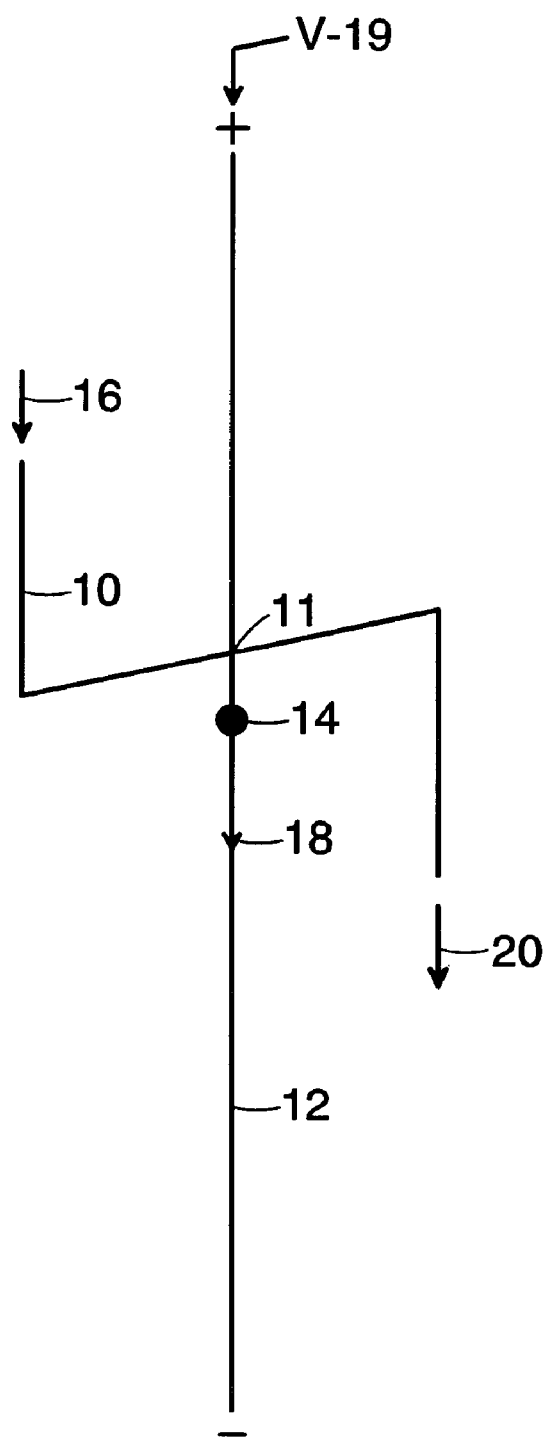
FIG. 1 is a schematic diagram of a sample plug formation device of the invention. A sample introduction channel forms a non-parallel juncture with a separation channel in which a sample plug is formed. The direction of sample flow is shown by arrows 16, 18, and 20.

The present invention provides for the automated formation of a sample plug which may be separated into its individual components and/or analyzed. As used herein, the term "sample" is intended to mean any source suspected to contain any component to be detected or identified, or any potentially reactive chemical entity. A sample can be "neat" or can be diluted with an appropriate solvent. Currently preferred samples include, but are not limited to, any biological specimen suspected to contain a component of interest. Samples suitable for use in the claimed invention include, but not limited to body fluids such as blood, serum, plasma, urine, cerebrospinal fluid, saliva, sweat, semen, tears, vaginal fluid, amniotic fluid, and ascites fluid.

As used herein, the term "component" is intended to mean any identifiable or detectable substance, or a substance susceptible to separation from other substances in a sample using an apparatus of the invention. Preferred components include, but are not limited to, chemical and biochemical moieties, such as proteins, peptides, nucleic acids, peptide hormones, non-peptide hormones, drugs of abuse, pharmaceuticals, microbial antigens, viral antigens, carbohydrates, polyclonal antibodies, monoclonal antibodies, anti-idiotypic antibodies, antibody fragments, enzyme substrates, enzyme inhibitors, biotin, receptors, ligands, inhibitors, and binding competitors. Components also may be bound to a probe, and in particular, a detectably-labeled probe. Common probes include polynucleotides, riboprobes and peptide nucleic acids (PNAs).

Broadly, the invention provides apparatus and methods for analysis of a microscale sample. However, any size sample may be analyzed with an appropriately sized sample analysis device of the invention using concepts and principles disclosed herein. An apparatus of the invention has a housing which defines two channels. The two channels intersect to form a junction. Sample is introduced into a first channel, the sample introduction channel. The sample introduction channel intersects a second channel, the separation channel. The channels may intersect at any angle to form the junction. The separation channel typically is longer than the length of the sample introduction channel. Preferably, the separation channel is greater than ten times longer than the sample introduction channel and more preferably, greater than one hundred times longer. If the difference in lengths of the sample introduction channel and the separation channel is not extremely large, the cross section of the sample introduction channel may be larger to compensate for the pressure drop, i.e., to reduce the pressure drop.

An apparatus of the invention further comprises a pressure control device to apply pressure gradients to the channels. The pressure control device itself may be a positive pressure source such as a peristaltic pump, or a vacuum source such as a vacuum pump. A vacuum source also may be an absorbant device such as a wick which draws liquid into a channel using surface tension (capillary action). However, the pressure control device may include a controllable pressure source, e.g., a vacuum source or a positive pressure source such as a peristaltic pump or a source of pressurized gas. Accordingly, the pressure control device may include hardware such as valves, manifolds, tubing and the like. The pressure control device also may include controllers such as any suitable microprocessor based programmable logic controller, personal computer controller, or the like for process control. A suitable controller includes features such as programmability, reliability, flexibility, and durability. The suitable controller includes various input/output ports used to provide connections to open and close valves, regulate and meter fluids, among other features. The controller also includes sufficient memory to store process recipes for desired applications. Of course, the type of controller used depends upon the particular application.

Application of a pressure gradient within the channels moves sample through the channels. The channels preferably are formed on a microfabricated solid, such as, e.g., a microchip. The separation channel may have sieving media, such as polyacrylamide as a viscous solution or a gel, disposed therein to facilitate separation and/or analysis. After separation, the sample components may be detected using a detector disposed along or near the end of the separation channel. The apparatus may be used to automatically perform assays such as, among others, immunoassays, enzyme assays, chemical assays, receptor assays and polynucleotide identifications.

An apparatus of the invention provides for the automated, uniform preparation of a sample plug through the use of vacuum and/or positive pressure on the sample introduction and separation channels. The sample introduction and separation channels define an injection system of a scientific instrument of the invention. As illustrated in FIG. 1, the sample introduction channel 10 forms a junction 11 with the separation channel 12. Alternately applying positive pressure and/or vacuum to the channels causes a sample plug 14 to form downstream of the junction in the separation channel 12. (It should be understood that FIG. 1 is a schematic representation and that in practice, the sample plug 14 is contained within the channels.) Arrows 16, 18, and 20 show the direction of sample flow. Voltage generator 19 may be used to apply a voltage gradient along the longitudinal axis of the separation channel. For example, a voltage gradient maay be applied while a pressure differential moves sample through the sample introduction channel in one type of sample plug formation process referred to as "stacking," more fully described below.

To assist in automating the methods described herein, another aspect of the invention is a scientific instrument which contains the sample analysis apparatus described above. The scientific instrument permits the efficient automation of the systems of the invention with its auxiliary devices and equipment. The scientific instrument also permits other apparatus, e.g., a sample delivery system, to be linked to the analysis systems of the invention to allow a functional design to suit the end users needs. For example, analytical instruments may be linked to a scientific instrument of the invention to permit analysis of samples, e.g., at given times in the reaction cycle. Analytical instruments useful in the invention will be well known to those skilled in the art and include , but we not limited to, mass spectrometry instruments, chromatography systems, and various detection instruments such as ultraviolet, infrared, fluorescent, and refractive indices detectors. Such a detector may be positioned away from the junction and in communication with the separation channel.

Other non-limiting examples of auxiliary instruments useful in the invention include diagnostic instruments for performing assays, and synthesizers for automating the production of particular compounds to become part of a sample. Such synthesizers include those capable of performing combinatorial syntheses which permit the screening of libraries of compounds with the delivery systems of the invention. All of the above instruments and devices may be operated manually in a step-wise fashion. However, full automation is preferred. As appreciated by a skilled artisan, automation preferably includes a microprocessor and/or computer which controls various aspects of the methods of the invention, but typically at least is in communication with the means for generating the pressure differentials.

Methods of the invention provide for the formation of a sample plug and, in certain embodiments, for separation of the components of that sample plug. The application of pressure/vacuum serves to push or pull the sample through the channels of the injection system of an apparatus of the invention. After a sample plug is formed in the separation channel, its components may be separated, preferably by electrophoresis. However, a metered sample plug may be transported to another analytical device for analysis without further separation. FIGS. 2A–2F illustrate the various stages of sample plug formation. Numerous means exist for introducing a sample into the apparatus, e.g., injection from a syringe or the like, or introduction from a sample delivery system known in the art. In another embodiment, an absorbent material, such as cotton, may be placed in the introduction channel. The absorbent material attracts sample into the sample introduction channel by capillary action. In another embodiment, an absorbent material may be placed in contact with the outlet of the sample introduction channel, e.g., above the channel, so that the absorbent material draws the sample through the sample introduction channel by creating a vacuum from surface tension (capillary action).

Figure 2F:
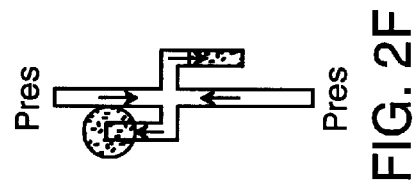
FIG. 2: A–F are schematic cross-sectional views of a device of the invention showing flow of sample through the channels at various stages during the practice of a method of the invention.
Figure 2E:
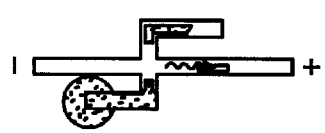
Figure 2D:
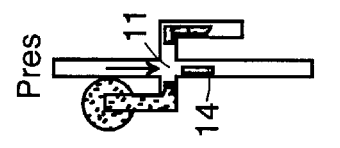
Figure 2C:
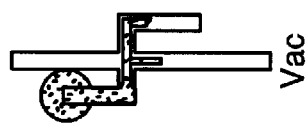
Figure 2B:
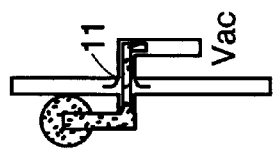
Figure 2A:
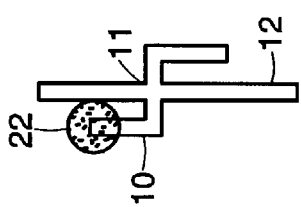

As shown in FIG. 2A, sample 22 is deposited in the sample introduction channel 10. In FIG. 2B, application of a first pressure differential, i.e., a vacuum, to the sample introduction channel opposite where the sample was introduced draws sample through the sample introduction channel and across the juncture 11 formed with the separation channel 12: In FIG. 2C, application of a second pressure differential, i.e., another vacuum, to the separation channel draws a portion of the sample into the separation channel.

Application of a pressure differential to the separation channel 12 for a specific interval reproducibly produces discrete sample plugs. In FIG. 2D, application of positive pressure to the separation channel from the direction opposite of sample 22 flow causes a plug of sample 14 to form downstream of the junction 11 while the remaining sample is moved to waste or back to the introduction location. In certain embodiments, the positive pressure may continue to move the sample plug through the separation channel to effect separation similar to operation of a chromatography column.

In a preferred embodiment, the separation channel contains a sieving medium for separation of the sample components based on charge or size. The sieving medium may comprise, for example, polyacrylamide, agarose, polyethylene oxide, polyvinyl pyrolidine, and methylcellulose. Other sieving media such as chromatography particles may be used depending on the particular application. In FIG. 2E, the components of the sample are moved electrophoretically along the separation channel and are separated by application of a voltage gradient along the longitudinal axis of the separation channel 12. Separation of the sample components is achieved by standard electrophoretic methods. Finally, subsequent to separation and/or analysis, FIG. 2F depicts positive pressure being applied from both directions along the separation channel to force the sample remnants out of the channels to cleanse the system.

It should be understood that the different pressure differentials used to form a sample plug in the separation channel may be adapted for a particular application. That is, whether vacuum and/or positive pressure are used, and in what sequence, depends upon the analysis to be conducted. Moreover, the timing, strength and location of the pressure differentials are variables which should be optimized using the general principles and concepts disclosed herein. For example, in one embodiment, the first pressure differential applied to the introduction channel is reduced prior to the application of the second pressure differential to the separation channel. However, the specific examples discussed and depicted herein are meant to illustrate, but in no way limit, the present invention.

One way to manipulate the composition of a sample plug formed using methods of invention is to vary the ionic strength of the media, e.g., buffer solutions, in each channel. In the example depicted in FIGS. 2A–2F, the ionic strengths of the media in the sample introduction channel and the separation channel were substantially equivalent. As a result, the sample plug formed is not concentrated or diluted with respect to the ionic or charged species present in the sample. That is, concentration of the charged species in the sample plug should be approximately equal to their concentration in the initial sample charged into the sample introduction channel.

However, a sample plug also may be formed using a process called "stacking," which concentrates the charged components, of a sample at the junction prior to sample plug formation. Basically, when an electric potential is applied axially along the separation channel while a pressure gradient moves a sample along the sample introduction channel, a region of increased ionic concentration results at the junction provided the medium in the sample introduction channel is at a lower ionic strength than the medium in the separation channel. This results in a sample plug which is more concentrated in one or more ionic species relative to the sample introduced in the sample introduction. Modulation of the applied voltage permits a desired sample concentration to be realized.

Figure 3F:
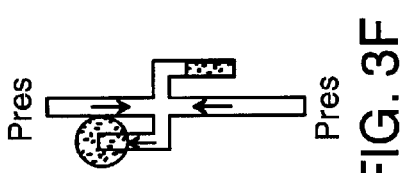
FIG. 3: A–F are schematic cross-sectional views of a device of the invention showing flow of sample through the channels with application of a "stacking" voltage along the separation channel.
Figure 3E:
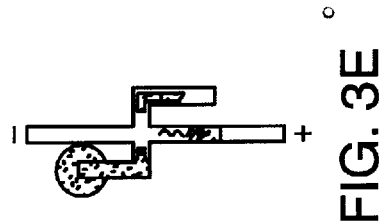
Figure 4D:
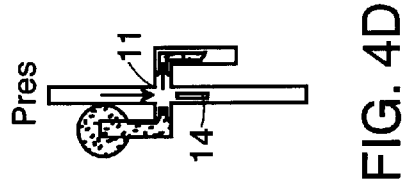
FIG. 4 shows a preferred embodiment of the invention which is a microchip assembly etched with a series of sample introduction channels and separation channels. The depicted microchip has connections which control the pressure and/or voltage through the channels.
Figure 3C:
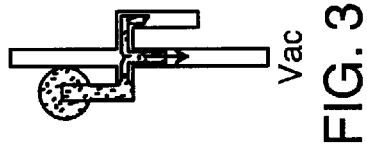
Figure 3B:
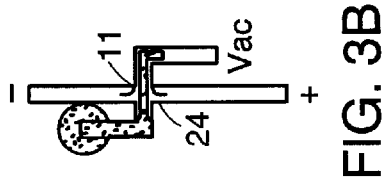
Figure 3A:
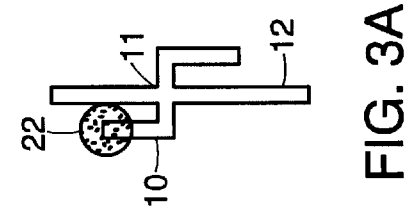

Referring to FIGS. 3A–3F, the method of sample plug formation referred to as "stacking" is depicted using an apparatus of the invention. FIGS. 3A–3F show a series of diagrams similar to those in FIGS. 2A–2F, except that the ionic strength of the media in the sample introduction channel 10 is lower than the ionic strength of the medium in the separation channel 12. In addition, a voltage gradient is applied to the separation channel 12 while a vacuum moves samplealong the sample introduction channel 10 as shown in FIG. 3B. As understood by a skilled artisan, ionic species moving in an applied electric potential from a lower ionic strength medium to a higher ionic strength medium will experience a decrease in their rate of movement due to a decreased electric field in the higher ionic strength medium. Accordingly, as shown in FIG. 3B, the ionic species "pile up" or concentrate at the interface 24 of the two differing ionic strength media. With the continuous flow of sample through the juncture, the ionic species in a sample may become highly concentrated at the interface 24. Subsequent to the appropriate amount of "stacking," the electric potential is removed and a pressure differential applied to the separation channel to form a sample plug which is concentrated in the ionic species of the sample as shown in FIGS. 3C and 3D. The remaining steps of the method, FIGS. 3E and 3F are as described above for FIGS. 2E and 2F.

The procedure of stacking may be useful to concentrate components in dilute samples so a detectable amount of the component or components of interest are transported through the separation channel. Alternatively, a sample medium may be diluted using "anti-stacking." Essentially the same procedure is practiced, however, the sample is in a higher ionic strength medium than is present in the separation channel. Accordingly, an optimized sample plug, e.g., its size and concentration of components, may be controlled by the above techniques, i.e., stacking, anti-stacking and non-stacking.

Figure 4:
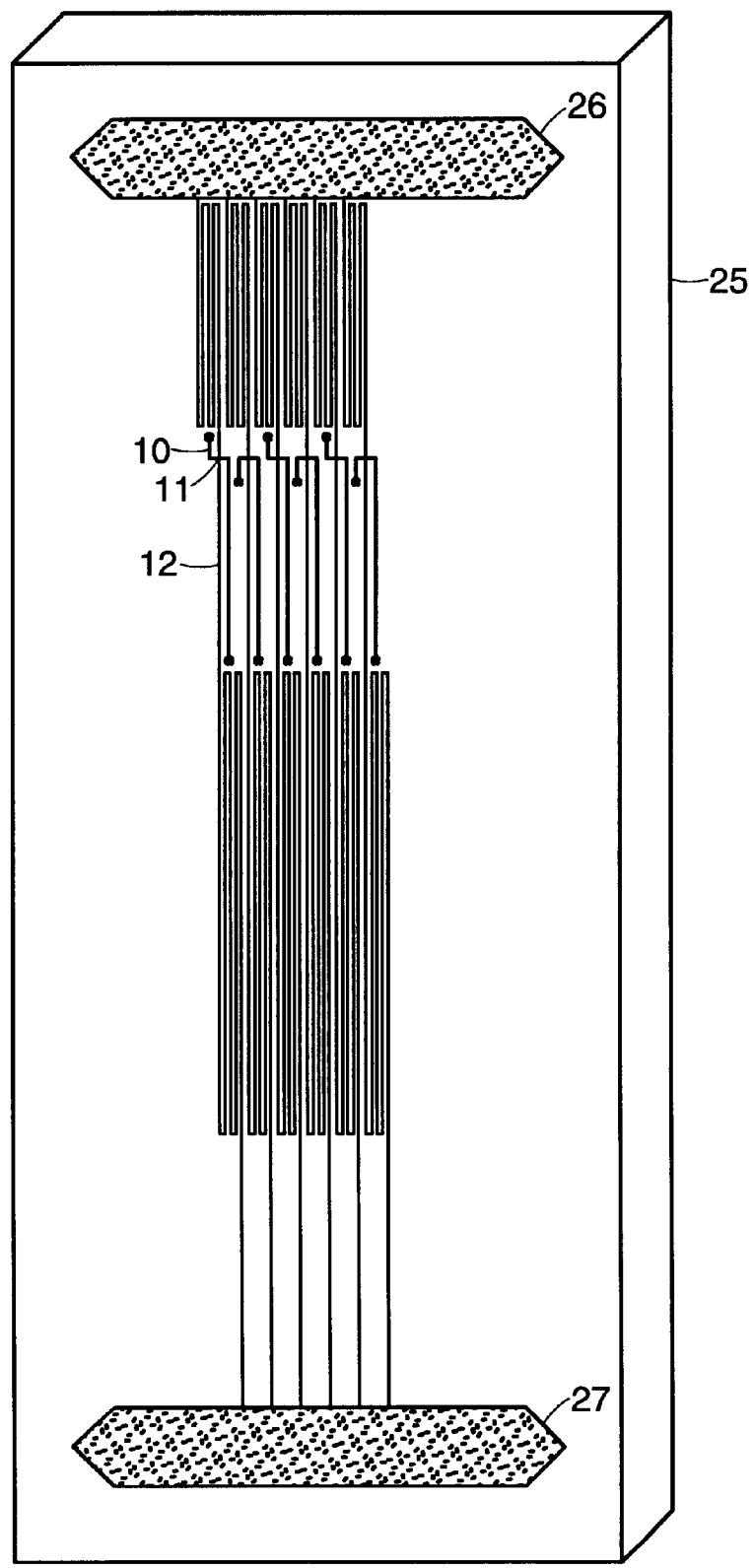

FIG. 4 illustrates a preferred embodiment of the invention. A microchip assembly 25 etched with a series of sample introduction channels 10 and separation channels 12 is shown. The channels meet to form a junction 11. As depicted, the microchip has a plurality of sample introduction and separation channels. The channels are between about 10 $\mu$m and about 100 $\mu$m in width and about 0.1 $\mu$m to about 1000 $\mu$m in depth. The microchip also has manifolds 26 and 27 for transporting a sample and/or reagents to and/or within the separation and sample introduction channels.

Microchips having sample introduction and separation channels can be designed and fabricated in large quantities from a solid substrate material. They can be sterilized easily. Silica is a preferred substrate material because of the well-developed technology permitting its precise and efficient fabrication, but other materials may be used, including polymers such as polytetrafluoroethylenes. The sample introduction and separation channels may be fabricated inexpensively in large quantities from a silica substrate by any variety of micromachining methods known to those skilled in the art. The micromachining methods available include film deposition processes, such as spin coating and chemical vapor deposition, laser fabrication or photolithographic techniques, such as UV or X-ray processes, and etching methods, which may be performed by either wet chemical processes or plasma processes. (See, e.g., Manz, et al., *Trends in Analytical Chemistry* 10:144–149 (1991).)

Channels of varying widths and depths can be fabricated with microscale dimensions. A silicon substrate containing fabricated sample introduction and separation channels may be covered and sealed with a thin anodically bonded glass cover. Other clear or opaque cover materials may be used. However, to anodically bond properly, one of the substrate or cover should be silica and the other silicon. Accordingly, for example, a silica and a silicon substrate may be sandwiched, or a silicon substrate may be sandwiched between two glass covers. The use of a transparent cover results in a window which facilitates dynamic viewing of the channel contents and allows optical probing of the channels either visually or by machine. Other fabrication approaches may be used.

Figure 5:
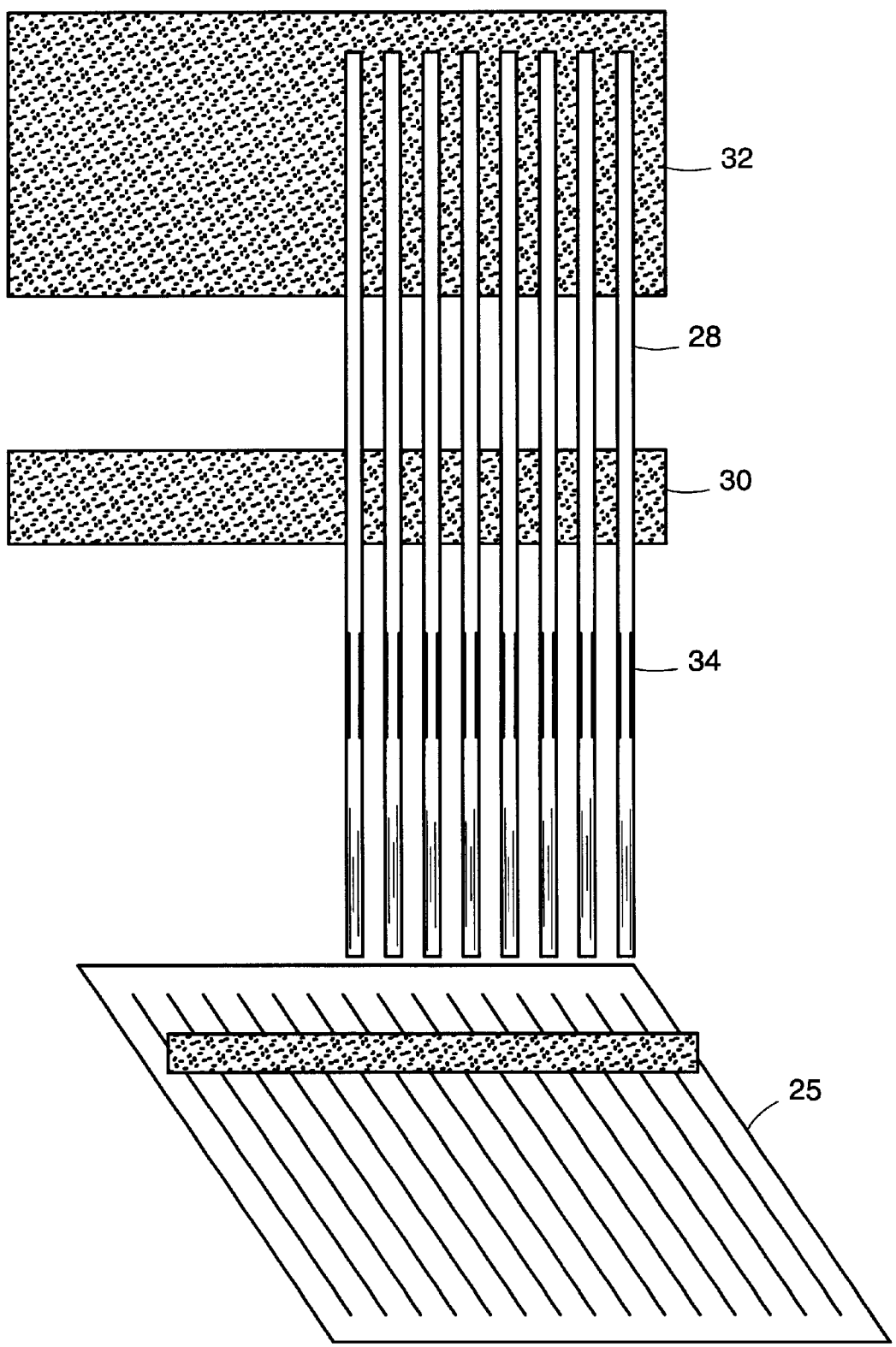
FIG. 5 shows a sample delivery system in association with a microchip assembly embodiment of the present invention as depicted in FIG. 4. The sample delivery system includes an array of capillaries pre-loaded with a set of chemical reagents and in association with a temperature control device. The capillaries are positioned over the microchip assembly and are used to deliver sample to the sample introduction channels of the microchip assembly.

Samples to be analyzed may be delivered to the sample plug formation device of the invention by sample delivery systems, such as disclosed in co-owned, co-pending U.S. patent application Ser. No. 09/293,314, entitled "Apparatus And Methods For Sample Delivery," which is incorporated by reference herein in its entirety. A preferred array of such sample delivery systems is shown in FIG. 5. An array of capillaries 28 are held by an array holder 30. The inner diameter of the capillaries preferably is from about 5 $\mu$m to about 1000 $\mu$m, and more preferably from about 20 $\mu$m to about 300 $\mu$m. Although dimensions are provide for substantially circular cross sectional areas of capillaries, similar cross sectional areas are preferred for non-circular channels, e.g., such as rectangular channels having a width and a depth.

One end of each of the capillaries is sealed and contacts a temperature control device 32. The capillaries also have an opening, which preferably is opposite the closed end. The capillaries may be made of, e.g., glass or plastic, and the temperature control device may be any commercially available or custom made heating and cooling device, e.g., a Peltier element. The capillaries further may contain chemical reagents 34 immobilized on their walls. Immobilization of the chemical reagents on the capillary walls may be accomplished by drying. The reagents may be delivered to the capillary by, e.g., injecting them into the capillary with a microneedle. Typically, the microneedle has a diameter smaller than the inside diameter of the capillary. Once the chemical reagents are in place, they may be dried by techniques known in the art. Alternatively, the reagents may be loaded hydraulically by heating and cooling to draw a solution containing the reagents into the capillary, drying the reagents at the desired location within the capillary, then washing those regions where reagents are not desired. The reagents also may be loaded by other techniques known in the art.

The chemical reagents immobilized in the capillaries may be binding proteins, ligands, receptors, antibodies or antigens for a component suspected to be contained in the sample. The reagents may additionally include buffers, surfactants, additives, excipients, carriers, haptans or other compatible molecules that facilitate or influence reaction with sample components.

The reagents also may comprise detectable moieties. As used herein, the term "detectable moiety" is intended to mean any moiety suitable for use in the claimed invention including, but not limited to: enzymes, fluorophores, biotin, chromophores, radioisotopes, colored particles, electrochemical or chemiluminescent moieties. A currently preferred detectable moiety is a fluorescent moiety, such as rhodamine. Other currently preferred detectable moieties include: fluorescein, cyanine dyes, coumarins, phycoerythrin, phycobiliproteins, dansyl chloride, and Texas Red.

A sample delivery system as described above may be positioned over the opening of a sample introduction channel of a microchip assembly 25 for delivery of a sample for analysis. In operation, the sample delivery systems pick up sample, allow the sample to react with the chemical reagents immobilized on their walls and then deliver the products of the reaction, if any, to the sample introduction channels of a device of the invention. As shown in FIG. 5, an array of such sample delivery systems simultaneously can deliver a plurality of samples to a plurality of sample introduction channels on a microchip assembly 25.

Modulation of temperature near the closed end of the capillaries by the temperature control device 32 controls the pick up and delivery of samples, i.e., the movement of sample within the capillaries. Since the capillaries are sealed at one end, heating and cooling the gas in the closed end of the capillaries causes that gas to expand or contract, respectively. When the gas is heated, the volume it occupies, and hence the pressure in the capillary, increases approximately according to the perfect gas law PV=nRT, where P is pressure, V is volume, n is the number of gas molecules, R is the constant 8.314 $JK^{-1}mol^{-1}$, and T is the temperature. Gas is therefore forced through the opening in the capillary when the gas is heated. The capillary then is submerged in the sample and cooled. Upon cooling, the gas in the capillary contracts and the sample enters the capillary. As the gas in the capillary contracts, the pressure in the capillary decreases. The pressure differential between the outside and inside of the capillary forces sample into the capillary.

Upon sufficient cooling, the sample contacts the chemical reagents immobilized on the capillary walls and reacts with those reagents. The time a sample is allowed to remain in contact with the reagents is determined by the reaction to be performed. Further heating and/or cooling of the capillary moves samples from a first location in the reactor to second and subsequent locations, where second or subsequent reactions take place. After the reaction is complete, reheating the capillary causes the gas to expand, forcing the sample from the capillary. If the capillary is positioned over the opening of a sample introduction channel of an apparatus of the invention, the sample is delivered directly to that apparatus for sample plug formation.

A sample delivery system used in conjunction with a sample analysis device of the invention may be used to conduct numerous types of chemical reactions. For example, the system and device may be used in diagnostic applications, such as blood testing (e.g., to identify blood components, or to detect/identify DNA in blood), immunoassays (e.g., to detect the presence of a specific antigen in a sample), or calorimetric or other assays (e.g. radiochemical, chemiluminescent, binding assays, and the like). The system and device may be used to detect toxins (e.g., bacteria, alcohol, drugs, viruses, organisms, metals, abnormal levels of physiological chemicals, and the like) or other components in a sample (e.g., a biological or environmental sample). A sample delivery system also may be used in chemical synthesis (e.g., in the manufacture of drugs, peptides, nucleotides, etc.). In addition, a sample delivery system may be used in numerous laboratory techniques, such as peptide or nucleotide sequencing, amplification, or modification.

Figure 6:
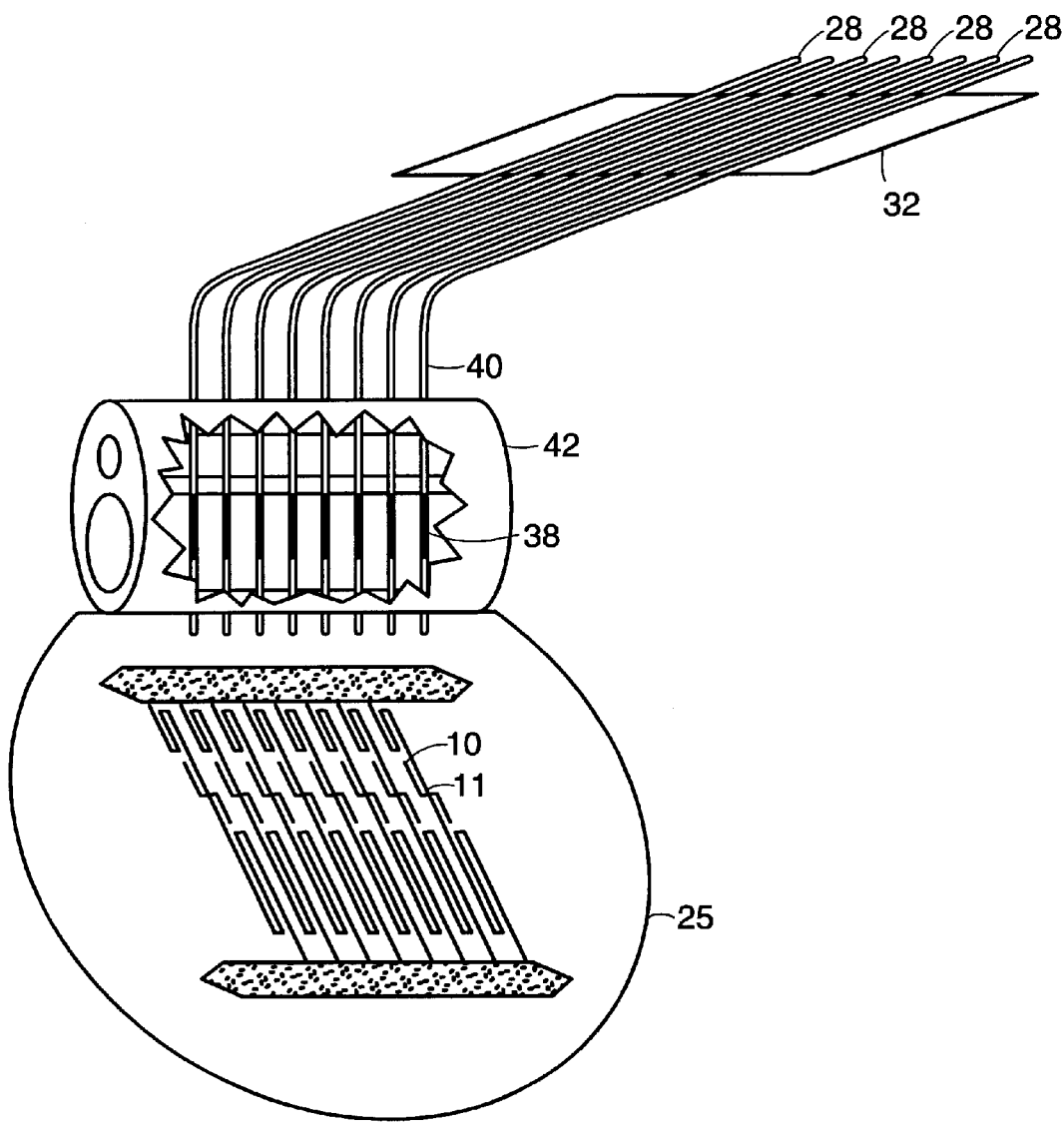
FIG. 6 shows an array of capillaries containing a first set of chemical reagents and a second set of chemical reagents. A temperature control device is shown in association with the capillaries. A second temperature control device for localized heating and cooling also is shown. The capillaries are positioned over a microchip assembly for delivery of samples to the sample introduction channels.

A sample delivery system which amplifies and aids in detecting target polynucleotide sequences also may be used to deliver sample to an apparatus of the invention. FIG. 6 shows an array of capillaries 28 in thermal association with a temperature control device 32. Each capillary has one end sealed which is near the temperature control device 32. The capillaries each contain a first set of chemical reagents 38 and a second set of chemical reagents 40 immobilized on the capillary walls. A second temperature control device 42, which has conduits for warm and/or cool gas or liquid, permits control of the temperature in a discrete portion of the capillary, e.g., the region containing the chemical reagents. The sample delivery systems shown are positioned over a microchip assembly 25 for depositing the reaction products at the sample introduction channels 10 of an apparatus of the invention.

Use of the second temperature control device allows for the temperature of the reactions to be controlled without affecting the temperature of the gas in the closed end of the capillary. As described above in discussing FIG. 5, heating the capillary causes the gas to expand and thus moves the sample within, or out of, the capillary. By heating a discrete portion of the capillary where the reagents and sample are located, the temperature of the reaction may be controlled without moving the sample within the capillary. Various insulators present within or exterior to the capillary may be used to maintain a sample stationary within the capillary while also permitting localized heating and/or cooling. That is, the insulators can thermally shield the gas near the closed end of the capillary to prevent its expansion or contraction.

In one embodiment of the invention, the first set of reagents 38 may be reagents for performing a polynucleotide amplification reaction, such as PCR. PCR is well known in the art. See, e.g., U.S. Pat. No. 5,330,892. In addition, other polynucleotide amplification reactions known in the art may be conducted using a reactor, including isothermal in vitro amplification of DNA using a restriction enzyme/DNA polymerase system, Walker, et al., *Proc. Natl. Acad. Sci. U.S.A.*, 89: 392–96 (1992), and ligase chain reaction ICR). Backman, *Clin. Chem.* 38: 457–58 (1992), each of which is incorporated by reference herein.

Reagents for performing PCR typically include a buffer, at least one primer, a polymerase, such as, e.g., Taq polymerase, and at least one nucleoside triphosphate. The choice of buffers, primers, and other components is within the skill in the art, depending upon characteristics of the sequence to be amplified (e.g., length, abundance in the sample, G/C content). A polymerase may be selected from the group consisting of Taq polymerase, *E. coli* DNA polymerase I, Klenow fragment of *E. coli* DNA polymerase I, T4 DNA polymerase, other available DNA polymerases, reverse transcriptase, and other enzymes, including heat-stable enzymes. The nucleoside triphosphates may include dCTP, dGTP, dATP or dTTP.

The second set of reagents 40 includes probes for binding to amplified target DNA. Probes for use in a reactor may be any DNA binding protein and may preferably be a complementary sequence, such as a riboprobe, a polynucleotide, or a PNA. It is preferable that the probes are detectably labeled. Preferred labels include radioisotopes, fluorescent or colorimetric labels, enzymatic labels, and molecular weight labels. A particularly preferred probe is a Peptide Nucleic Acid or PNA. Peptide nucleic acids are well-known DNA mimics with a neutral polyamide backbone on which the nucleic acid bases are attached in the same manner as they are attached to the phosphate backbone of DNA. See, Egholm, et al., *Nature*, 365: 566–568 (1993); Oerum, et al., *Nucl. Acids Res.*, 23: 5332–36 (1993); Pluskal, et al., *The FASEB Journal*, Poster #35 (1994); *Practical PNA: Identifying Point Mutations by PNA Directed PCR Clamping*, PerSeptive Biosystems Vol. 1, Issue 1 (1995). Peptide nucleic acid synthons and oligomers are commercially available. (PerSeptive Biosystems, Inc., Framingham, Mass.). See, also, PCT publications EP 92/01219, EP 92/01220, and U.S. Ser. No. 92/10921, incorporated by reference herein.

Peptide nucleic acid probes typically form more stable duplexes with DNA as compared to DNA/DNA duplexes. Additionally, because PNA/DNA complexes have a higher thermal melting point than the analogous DNA/DNA duplexes, use of PNA probes can improve the reproducibility of blotting assays.

Fluorescein or biotin labeled PNA probes are synthesized on an Expedite Nucleic Acid Synthesis System (PerSeptive Biosystems). Spacer units of 8-amino-3,6-dioxaoctanoic acid (-o-) are added to resin-bound PNA before reacting activated esters of biotin (Bio) or fluorescein (Flu), such as dimethoxytritylbiotin ester of 1-(4'-nitrophenyl)pyrazolin-5-one (DMTr-bio-HPP) or 5,6-carboxyfluorescein-N-hydroxysuccinimide, with the PNA. After labeling, PNAs are cleaved from the resin and any protecting groups are removed using, for example, a TFMSA/TFA/m-cresol/thioanisole (2:6:1:1) mixture for two hours at room temperature. Labeled PNA is precipitated by addition of anhydrous ether. Crude PNA precipitate is purified by high performance liquid chromatography on a Deltapack C18 column (Waters), and by Sephadex G-25 to remove fluorescent impurities.

Immobilization of the chemical reagents on the capillary walls may be accomplished by drying. The reagents may be delivered to the capillary by, for example, injecting them into the capillary with a microneedle. Other techniques for introduction of reagents into a capillary or channel have been discussed previously or would be known to skilled artisans. After the chemical reagents are in place, they are dried by, for example, blowing warm air over them or placing them in an oven. The PCR reagents may be dried in a carbohydrate matrix, such as, for example, dextran or trehalose, prior to immobilization on the capillary walls. Each set of chemical reagents are preferably dried in separate rings around the capillary walls.

In operation, the sample suspected of containing a target polynucleotide sequence is brought into contact with the first set of reagents in the capillaries (i.e., the PCR reagents) by heating the closed end of the capillary to expel gas, placing the capillary in the sample, and then cooling the closed end of the capillary to contract the gas and thus draw in the sample. Once the capillary is sufficiently cooled, the sample contacts the first set of chemical reagents. The second temperature control device 42, placed at a position on the reactor occupied by the PCR reagents, controls thermocycling. The second temperature control device 42 first increases temperature at the position occupied by PCR reagents in order to denature double-stranded DNA in the sample. The same, or a different, temperature control device then cools the reactor region containing the PCR reagents to cause annealing of PCR primers to single-stranded template strands. Heating to a temperature intermediate between that for denaturation and that for annealing causes primer extension. A number of such cycles are repeated until the reaction is complete. The number of PCR cycles, as well as the precise reagents used vary depending upon the amount of available template DNA, reaction efficiency, and other known factors. General protocols and parameters for PCR are known, and are available, for example, in *Short Protocols in Molecular Biology*, 15-1–15-40 (Ausebel, et al., eds. 1995), incorporated by reference herein.

Once PCR is complete, the amplified target sequence is brought into contact with the set of complementary probes by cooling the gas in the closed end of the capillary with the temperature control device 32. The skilled artisan recognizes that a single temperature control device may be used to heat or cool the capillary in order to move sample, and to heat or cool discrete capillary regions for PCR. However, as shown in FIG. 6, separate temperature control devices are preferred. The set of probes may comprise multiple copies of a single probe that is known to hybridize with at least a portion of the amplified target, or the set may comprise a plurality of different probes, some hybridizing to portions of the target, some being non complementary to the target.

The sample, comprising amplified nucleic acid, is brought into contact with the probes by cooling the capillary in order to cause sample to move up (away from the point of gas/sample entry) and into contact with the region of the capillary comprising probes, as referred to above. Sample is allowed to incubate with the set of probes for a time sufficient to cause hybridization to a desired level of stringency. The hybridization parameters (i.e., time, buffer, salt concentration, temperature, etc.) are determined based upon sequence length, G/C content, desired stringency, and other criteria known to the skilled artisan. See, e.g., Ausubel, supra at 6–7. Once a desired level of hybridization has been achieved, sample (including hybrid duplex formed between target and probe) is eluted into a sample plug formation device of the invention by further heating the reactor. Eluted sample may then be washed to remove excess (unbound) label. The target polynucleotide sequence is then detected using a sample analysis apparatus of the invention to determine the presence and/or amount of target DNA.

Figure 7:
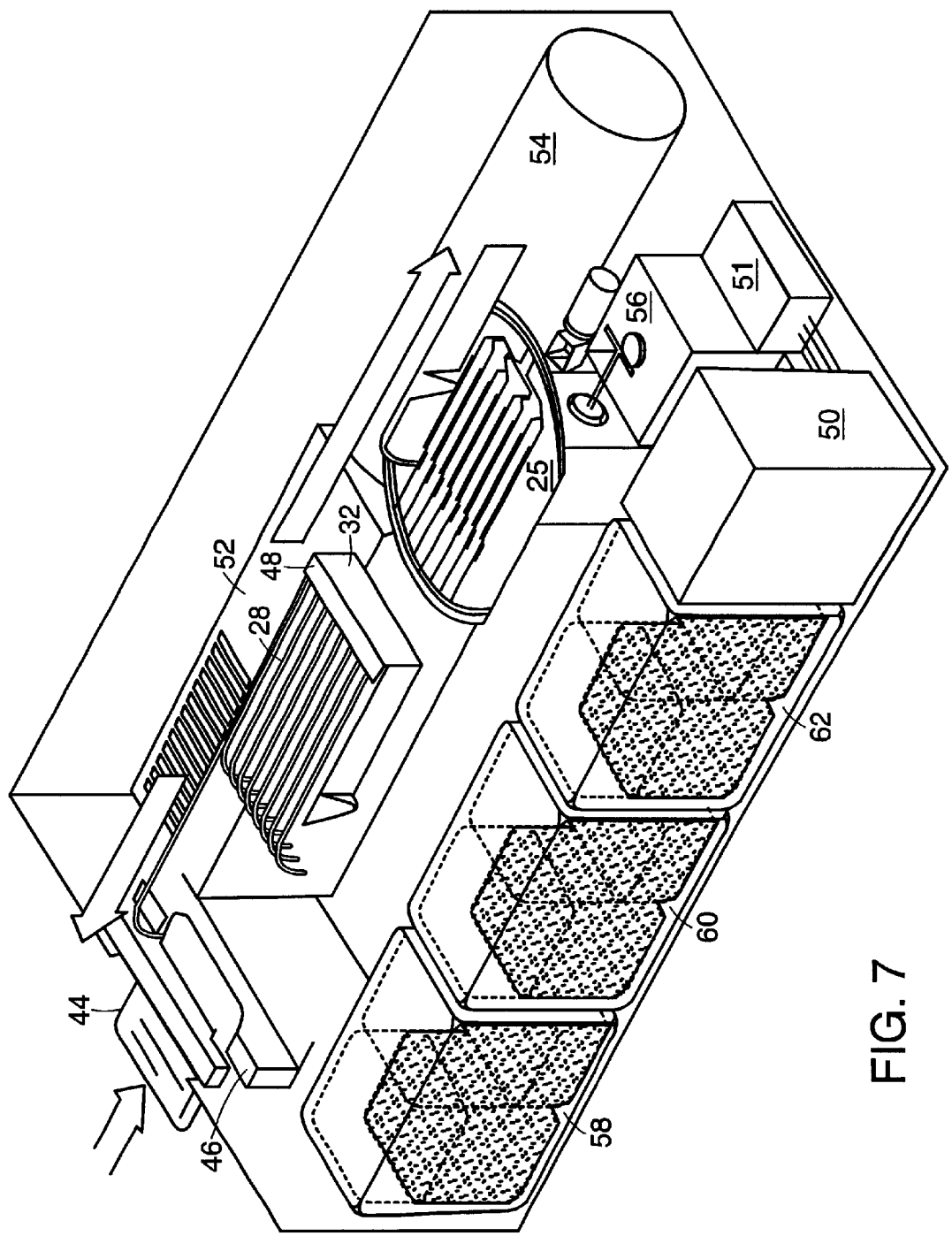
FIG. 7 depicts a scientific instrument of the invention which includes an integrated sample delivery system, sample plug formation device and other related equipment for performing rapid, automated analysis of microscale samples.

The sample analysis apparatus for injection, separation of sample components and detection of labeled components may be combined with a sample delivery device as described above for the rapid, automated analysis of biological samples without the complex machinery, time and biohazard exposure inherent in existing systems. FIG. 7 shows an integrated sample analysis apparatus and reactor array. The integrated device contains a sample card 44 having a membrane onto which a sample, such as, for example, blood is deposited. The card may be, e.g., an IsoCode™ card (Schleicher & Schuell, King, N.H.). The card may contain chemical reagents for lysing the cells of the sample deposited on the card membrane. The lysate then is dried by oven 46, thereby fixing the DNA from the lysed cells to the card membrane. The integrated device further comprises reactors 48, as described above with respect to FIG. 5 or FIG. 6. The device contains a microchip assembly 25 having sample introduction and separation channels, which are connected to pressure/vacuum unit 50, high voltage power supply 52, and high pressure cartridge 54.

Near the end of the microchip assembly's separation channels is an optical detection module 56. The optical detection module detects the presence of detectable moieties bound to the component of interest in the sample. Detection can be achieved by methodologies including, but not limited to: absorbance of ultraviolet radiation, absorbance of visible radiation, fluorescence, refractive index, Raman or mass spectrometry, electrochemistry, and conductivity. Detection by fluorescence is preferred. Fluorescence detection using this module involves a microchip laser beam, which scans across the channels of the microchip.

The integrated device further comprises a sterile deionized water unit 58, a sieving gel buffer unit 60, and a micro-channel reconditioning solution unit 62. Each of these three units as depicted is divided into two halves with one half containing the fresh solutions and the other half containing waste solutions.

In operation, a sample is deposited onto the membrane of the sample card 44, and the card is inserted into the integrated device, as shown in FIG. 7. The cells in the sample are lysed by the chemical reagents contained in the membrane. The cellular DNA, or other sample components, are then dried onto the membrane by heating with oven 46. At this point the card can be removed and archived, or it can be used in continued processing. Alternatively, a Guthrie paper dried blood blot may be used to deposit the sample.

After drying of the sample to the card, the card membranes are steam heated using sterile deionized water from unit 58 so as to extract the sample components into a small quantity of liquid. The capillaries of the reactors 48 are then heated to expel gas, moved into position over the membranes, and dipped into the liquid containing the sample. Upon cooling of the capillaries, the gas in the closed end of the capillaries contracts and sample is drawn into the capillaries. The capillaries are preferably pre-loaded with the reagents specific for the immunoassay or polynucleotide detection to be performed, as described above.

The sample once reacted in the capillaries, as described above, is deposited in the sample introduction channels of the microchip assembly 25. The capillaries move over so that they are positioned above the sample introduction channels. The capillaries are then heated by temperature control device 32 so that gas inside the closed end of the capillary expands and forces sample out of the capillary, as described above with respect to FIG. 5 and FIG. 6. Once used, the sample delivery systems can be disposed of and new systems containing reagents for the next reaction of interest can be inserted into the integrated device.

Once deposited at the sample introduction channel of the microchip assembly, pressure/vacuum unit 50 is used to create a pressure gradient inside the sample introduction and separation channels of the microchip, and thereby inject the sample into the separation channel, as described above with respect to FIG. 2. The pressure control device (pressure/vacuum unit 50) includes any suitable microprocessor based programmable logic controller, personal computer controller, or the like for process control, as shown generally at 51. High voltage power suply 52 (i.e., a voltage generator) may also be used to apply a voltage gradient to the separation channel to perform the stacking technique as described above with respect to FIG. 3.

After formation of the sample plug in the separation channel, high voltage power suply 52 is used to apply a voltage axially along the separation channel of the microchip so as to separate the components of the sample. A sieving medium is pre-loaded into the channels of the microchip. The buffer from unit 60 is injected into the separation channels prior to formation of the sample plug.

As the samples reach the end of the separation channel, optical detection module 56 is used to detect the presence of the detectable moieties attached to the sample components within the separation channels. For polynucelotide identifications, the results of the optical detection are compared against data produced from genotyping experiments. This data is in the form of intensity vs. time graphs that are electronically searchable in determining matching similarity.

After performance of the analysis pressure from high pressure cartridge 54 is used to apply pressure at both ends of the separation channel so as to cleanse the channels of the microchip assembly. The channels are then reconditioned using reconditioning solution from unit 62. The microchip assembly can then be reused in subsequent analyses. Alternatively, the microchip assembly may be disposed of.

Compared to methods known in the art, a sample plug formation device of the invention uses pressure differentials to form a sample plug for separation and/or analysis. Advantages of the present invention include the ability to form and separate a sample plug containing non-ionic species, and the ability to form a sample plug without application of an electric field so that the surface characteristics of and the medium in the channel do not affect greatly sample plug formation. Accordingly, the present invention offers several advantages over plug formation devices and methods known in the art.

Additionally, when used in conjunction with a sample delivery system described above, further advantages are realized. Compared to the use of conventional volume controllers such as syringes and pumps, a thermally-controlled sample delivery system has fewer moving parts which may wear out or require extensive maintenance. Moreover, since the sample delivery system may be independent of an analytical instrument, other benefits are realized. For example, the sample delivery channels can be made of low cost materials such as plastic capillary tubing since optical quality or integrated electrodes are not required. Accordingly, single use of a channel is attractive which can eliminate a cleaning step and/or cross-contamination.

In addition, since the channels typically are not used directly in an analytical technique, the channels may be readily moveable and have a higher degree of tolerance for positioning with a sample plug formation device of this invention. That is, since the detection system of an analytical device typically remains stationary, the optical alignment of a liquid detection capillary needs to be done once for optimal accuracy during the analysis of a plurality of samples. Furthermore, if the sample delivery system contains a chemical reagent and is used to perform a reaction, any particulates present or formed during the reaction easily can be filtered prior to introduction of the reaction products to a sample plug formation device thereby preventing clogging and/or inaccurate analysis. These above features permit simple and inexpensive automation robotics to be used.

Compared to using traditional systems which rely on capillary action to deliver, mix and/or react chemicals, a sample delivery system of the invention exhibits several advantages. The surface of a channel of a sample delivery system of the invention may be hydrophilic or hydrophobic in contrast to a capillary action surface which requires a hydrophilic surface. Also with respect to the surface of the channel, the reproducibility of sample solution metering is less dependent of the surface characteristics and sample constituents. In addition, the sample delivery system of the invention allows direct control over the metering of samples and reagents, and permits bubble segregation to be practiced routinely. These benefits not only are achieved by the sample delivery system described above, but also with respect to a sample plug formation device of the invention which uses pressure differentials.

Compared to electro-osmotic flow for delivering, mixing and/or reacting chemicals, a sample delivery system which uses pressure exhibits some of the same advantages compared to using capillary action discussed above, i.e., surface characteristics and reproducibility of solution metering. Moreover, the sample delivery system typically is unrestricted in its solution composition for conducting analysis and/or chemical reactions. That is, variables such as pHR ionic strength, buffer composition, chemical additives and solvents often are unlimited depending upon the particular application. These variables typically are restricted for effective electro-osmotic flow to occur. Again, as mentioned above, these benefits not only are realized with the sample delivery system described above, but also with respect to a sample plug formation device of the invention which uses pressure differentials.

Therefore, as described and illustrated above, the present invention allows for high speed analysis of microscale biological samples without the complexity, time, labor and biohazard exposure of conventional techniques. Additional aspects and embodiments of the invention are apparent upon consideration of the foregoing disclosure. Accordingly, the scope of the invention is limited only by the scope of the appended claims.

The invention may be embodied in other specific forms. What is claimed is:

1. A sample plug formation device comprising:
   a housing defining
      a separation channel comprising a longitudinal axis, and
      an introduction channel which forms a juncture with the separation channel;
   a pressure control device independently in communication with the separation channel and the introduction channel wherein
      a first pressure differential applied to the introduction channel transports a sample to the juncture, and
      a second pressure differential applied to the separation channel transports a portion of the sample in the juncture into the separation channel to form a sample plug; and
   a voltage generator in communication with the separation channel, wherein the voltage generator is adapted to apply an electric potential along the longitudinal axis.

2. The sample plug formation device of claim 1 further comprising a separation medium disposed within the separation channel.

3. The sample plug formation device of claim 1 wherein the housing comprises a microfabricated solid.

4. The sample plug formation device of claim 1 wherein the introduction channel and the separation channel independently have a mean diameter within the range of about 0.1 $\mu$m to about 1000 $\mu$m.

5. A scientific instrument comprising the sample plug formation device of claim 1.

6. The scientific instrument of claim 5 further comprising a computer in communication with the pressure control device to control the pressure control device.

7. The scientific instrument of claim 5 further comprising a detector spaced apart from the junction and in communication with the separation channel to detect a chemical component.

8. A method for forming a sample plug comprising the steps of:
   (a) providing a sample plug formation device comprising:
      a housing defining
         a separation channel comprising a longitudinal axis, and
         an introduction channel which forms a juncture with the separation channel; and
      a pressure control device in communication with the separation channel;
   (b) applying a first pressure differential to the introduction channel to transport a sample in communication with the introduction channel to the juncture;
   (c) applying a second pressure differential to the separation channel to transport a portion of the sample in the junction into the separation channel to form a sample plug; and
   (d) applying an electric potential along the longitudinal axis of the separation channel.

9. The method of claim 8 wherein the first pressure differential applied to the introduction channel is reduced prior to the application of the second pressure differential to the separation channel.

10. The method of claim 8 further comprising applying an electric potential along the longitudinal axis during step (b).

11. The method of claim 6 further comprising the step of analyzing for a component in the sample plug.

12. The method of claim 8 further comprising the step of applying positive pressure to the separation channel to move the sample plug along the separation channel.

13. The method of claim 12 wherein applying positive pressure separates components in the sample plug.

14. The method of claim 13 further comprising the step of analyzing for a component in the sample plug.

15. The method of claim 8 wherein applying the second pressure differential to the separation channel is for a specified interval.

16. A scientific instrument comprising:
   a microfabricated solid comprising,
      a housing defining
         a separation channel comprising a longitudinal axis,
         an introduction channel which forms a juncture with the separation channel, and
         a pressure control device independently in communication with the separation channel and the introduction channel wherein
            a first pressure differential applied to the introduction channel transports a sample to the juncture, and
            a second pressure differential applied to the separation channel transports a portion of the sample in the juncture into the separation channel to form a sample plug;
   a voltage generator in communication with the separation channel to apply an electric potential along the longitudinal axis;
   a computer in communication with the pressure control device to control the pressure control device; and
   a detector spaced apart from the junction and in communication with the separation channel to detect a chemical component.

17. The scientific instrument of claim 16 wherein the detector is an optical detector.

* * * * *